(12) United States Patent
Mandich et al.

(10) Patent No.: US 8,366,796 B2
(45) Date of Patent: Feb. 5, 2013

(54) MODULAR AND DISTRIBUTED METHODS AND SYSTEMS TO CONVERT BIOMASS TO SYNGAS

(75) Inventors: Mitchell Mandich, Palo Alto, CA (US); William B. Schafer, III, Boulder, CO (US)

(73) Assignee: Range Fuels, Inc., Denver, CO (US)

( * ) Notice: Subject to any disclaimer, the term of this patent is extended or adjusted under 35 U.S.C. 154(b) by 959 days.

(21) Appl. No.: 12/166,117

(22) Filed: Jul. 1, 2008

(65) Prior Publication Data
US 2009/0013601 A1 Jan. 15, 2009

Related U.S. Application Data

(60) Provisional application No. 60/948,661, filed on Jul. 9, 2007, provisional application No. 60/948,663, filed on Jul. 9, 2007.

(51) Int. Cl.
*C10J 3/00* (2006.01)
*B01J 7/00* (2006.01)
*B01J 8/00* (2006.01)
*C01B 3/36* (2006.01)
*C01B 6/24* (2006.01)

(52) U.S. Cl. ............ 48/210; 48/197 R; 48/61; 423/644; 423/648.1; 422/625

(58) Field of Classification Search .......... 48/197 R
See application file for complete search history.

(56) References Cited

U.S. PATENT DOCUMENTS

| | | | |
|---|---|---|---|
| 4,171,461 A | 10/1979 | Bartish | |
| 4,233,466 A | 11/1980 | Fiato | |
| 4,253,987 A | 3/1981 | Fiato | |
| 4,277,634 A | 7/1981 | Walker | |
| 4,371,724 A | 2/1983 | Lin et al. | |
| 4,374,285 A | 2/1983 | Lin et al. | |
| 4,409,405 A | 10/1983 | Lin et al. | |
| 4,424,384 A | 1/1984 | Lin et al. | |
| 4,530,700 A | 7/1985 | Sawyer et al. | |
| 4,699,632 A | 10/1987 | Babu et al. | |
| 5,607,487 A | 3/1997 | Taylor | |
| 5,707,408 A | 1/1998 | Kudo | |
| 6,863,878 B2 | 3/2005 | Klepper | |
| 7,196,239 B2 | 3/2007 | Van Egmond et al. | |
| 2002/0037938 A1* | 3/2002 | Luo et al. | 518/716 |
| 2007/0205092 A1 | 9/2007 | Klepper | |

OTHER PUBLICATIONS

Hironori Arakawa at al., "Selective Synthesis of Ethanol Over Rh-Ti-Fe-Ir/SiO2 Catalyst at High Pressure Syngas Conversion", Chemistry Letters, pp. 881-884, Mar, 11, 1985.
Dr. Suresh P. Babu, "Observations on the Current Status of Biomass Gasification", http://www.gastechnology.org/webroot/app/xn/xd.aspx?it=enweb&xd=iea/publications.xml, May 2, 2005.

(Continued)

*Primary Examiner* — Matthew Merkling
(74) *Attorney, Agent, or Firm* — O'Connor & Company; Ryan P. O'Connor (57) ABSTRACT

The present invention provides modular and distributed methods and systems to convert biomass feedstocks into synthesis gas (syngas). The syngas can then be turned into liquid chemicals and fuels such as ethanol. The modular units of the invention bring the conversion process to the biomass source, thereby minimizing feedstock transportation costs. The modules are capable of being connected to, and/or disconnected from, each other to easily adjust the overall feedstock capacity. The present invention also provides methods and systems to determine an optimal number and distribution of modular conversion units spatially located within a region of land. The disclosed methods and systems are flexible, efficient, scalable, and are capable of being cost-effective at any commercial scale of operation.

8 Claims, 11 Drawing Sheets

OTHER PUBLICATIONS

P.C. Badger, Processing Cost Analysis for Biomass Feedstocks, Oak Ridge National Laboratory, Environmental Sciences Division, Bioenergy Systems Group, Oak Ridge, TN USA, Report ORNL/TM-2002/199, Oct. 2002.

Phillip C. Badger et al., "Use of Mobile Fast Pyrolysis Plants to Density Biomass and Reduce Biomass Handling Costs—A Preliminary Assessment", Biomass & Bioenergy 30 (Jan. 4, 2006) 321-325.

R. Bain, "Small Modular Biopower Initiative Phase I Feasibility Studies Executive Summaries", NREL Report No. NREL/TP-570-27592, Feb. 2000.

E. Chynoweth, "Mixing and Matching Modular Pumps," Process Engineering (London), vol. 68, No. 9, pp. 77-79 (Sep. 1987).

Department of Energy (DOE) by the National Renewable Energy Laboratory (NREL), "Biomass FactSheet: Small Modular Biomass Systems", DOE/GO-102002-1676, Dec. 2002.

Division of Chemical Reaction Engineering, KTH—Kungl. Tekniska Högskolan, "Torrefied Wood an Alternative to Charcoal for Reducing Deforestation", http://hem.fyristorg.com/zanzi/torrefaction.html, Feb. 2001.

John L. Falconer et al., "Zeolite Membrane Research", http://www.colorado.edu/che/FalcGrp/research/zeolite.html (1996).

K. Goerner et al., "Design and Operation of a Modular Plant for Biomass Usage and Thermal Treatment of Wastes", paper prepared for Power-Gen Europe 2004 held in Barcelona, Spain (May 25-27, 2004).

Hames, B. et al., "Biomass Rapid Analysis Network", National Renewable Energy Laboratory, brochure NREL/FS-510-34724, Oct. 2003.

Jianil Hu et al., "Conversion of Biomass-Derived Syngas to Alcohols and C2 Oxygenates Using Supported Rh Catalysts in a Microchannel Reactor", Catalysis Today, vol. 120, pp. 90-95, Sep. 6, 2006.

Masaru Ichikawa et al., "Mechanism of Syngas Conversion Into C2-Oxygenates Such as Ethanol Catalysed on a SiO2-Supported Rh-Ti Catalyst", J. Chem. Soc., Chem. Commun., pp. 321-323 (1985).

Hongtao Ma et al., "Temperature-Programmed Surface Reaction Study on C2-Oxygenate Synthesis Over SiO2 and Nanoporous Zeolitic Material Supported Rh-Mn Catalysts", Surf. Interface Anal., vol. 32, pp. 224-227, Jan. 8, 2001.

"Mixed Alcohols From Syngas Over Moly Catalysts", Proc. 9th Intern. Cong. Catal., vol. 2, pp. 626-633 (1988).

Nexant Inc., "Equipment Design and Cost Estimation for Small Modular Biomass Systems, Synthesis Gas Cleanup, and Oxygen Separation Equipment. Task 1: Cost Estimated of Small Modular Systems", Subcontract Report No. NREL/SR-510-39943, May 2006.

R.Bruce North, "Universal Modular Platform", Proceeding of the 9th Middle East Oil Show & Conference, Society of Petroleum Engineers Middle East Oil Show, vol. 2, pp. 83-92 (Mar. 11-14, 1995).

S. Phillips et al., "Thermochemical Ethanol via Indirect Gasification and Mixed Alcohol Synthesis of Lignocellulosic Biomass", NREL Technical Report/TP-510-41168 (Apr. 2007).

Donald R. Peterson et al., "Modular Biomass Power Plant Feasibility Study", Lumberjack Resource Conservation and Development Council, Inc. (Sep. 2005).

Jose G. Santiesteban et al., "Mechanism of C1-C4 Alcohol Synthesis Over Alkali/MoS2 and Alkali/Co/MoS2 Catalysts", Proc. 9th Intern. Cong. Catal., 2, 561-568 (1988).

B.W. Schug et al., "Design of Standardized, Modular, Chemical Processes", Computers & Chemical Engineering, vol. 20, S435-S441, 1996.

A.I. Sorokin et al., "Modular Technological Processes in the Manufacture of Parts", Soviet Engineering Research, vol. 60, No. 11, pp. 20-21 (1989).

P.L. Spath et al., Technical Report, "Preliminary Screening—Technical and Economic Assessment of Synthesis Gas to Fuels and Chemicals with Emphasis on the Potential for Biomass-Derived Syngas", NREL Report No. NREL/TP-510-34929, Dec. 2003.

G. Van Der Lee et al., "On the Selectivity of Rh Catalysts in the Formation of Oxygenates", Journal of Catalysis, vol. 98, pp. 522-529 (1986).

International Search Report and Written Opinion dated Oct. 31, 2008 for PCT Application No. PCT/US2008/069065.

* cited by examiner

MODULAR AND DISTRIBUTED METHODS AND SYSTEMS TO CONVERT BIOMASS TO SYNGAS

PRIORITY DATA

This patent application claims priority under 35 U.S.C. §120 from U.S. Provisional Patent Application Nos. 60/948,661 and 60/948,663 for "Modular and Distributed Methods and Systems to Convert Biomass to Syngas," both disclosures of which are hereby incorporated by reference herein for all purposes.

FIELD OF THE INVENTION

This invention relates to flexible, efficient, and scalable methods and systems to convert carbonaceous materials such as biomass into synthesis gas, which in turn can be converted into liquid products such as ethanol.

BACKGROUND OF THE INVENTION

Synthesis gas (hereinafter referred to as syngas) is a mixture of hydrogen ($H_2$) and carbon monoxide (CO). Syngas is essentially a gaseous mixture of stable molecules that contain the elements carbon (C), hydrogen (H), and oxygen (O), arguably the three most-important elements for sustaining life. Syngas is a platform intermediate in the chemical and biorefining industries and has a vast number of uses, as is well-known. Syngas can be converted into alkanes, olefins, oxygenates, and alcohols. These chemicals can be blended into, or used directly as, diesel fuel, gasoline, and other liquid fuels. Syngas can also be directly combusted to produce heat and power.

Syngas can be produced, in principle, from virtually any material containing C, H, and O. Such materials commonly include fossil resources such as natural gas, petroleum, coal, and lignite; and renewable resources such as lignocellulosic biomass and various carbon-rich waste materials. It is preferable, however, to utilize a renewable resource to produce syngas because of the rising economic, environmental, and social costs associated with fossil resources.

There exist a variety of conversion technologies to turn carbon-containing feedstocks into syngas. Typical approaches utilize a combination of one or more steps comprising gasification, pyrolysis, steam reforming, and partial oxidation. As is recognized in the art, various advantages can be realized depending on the specific technology and process configuration selected.

In the chemical-process industries, including biomass refining, it is widely held that economies of scale are realized as processes are scaled up. While certain unit operations, such as filtration, tend to scale linearly, many common units such as reactors, holding tanks, and distillation columns tend to scale with a scale-up exponent n less than unity. Typically n=0.6–0.8, meaning that a doubling of capacity equates to something less than a doubling of capital cost. For example, when the scaling exponent n=0.6, the expected capital cost for a doubling of capacity is just 50% more than the base case ($2^{0.6}=1.5$). One reason for such economy of scale is that capacity tends to increase with volume, but costs for materials of construction tend to increase with surface area. Mathematically, this phenomenon predicts that the ratio of materials costs would increase to the two-thirds power with the ratio of volumes; indeed, n=2/3 is fairly typical.

For capital-intensive unit operations, there is thus economic pressure to make units as large as technically and practically possible. There are, however, several drawbacks to constructing massive-scale plants, especially for processing biomass.

First, there can be engineering uncertainties associated with scale-up. Even when a pilot plant is constructed and operated, the jump to the manufacturing scale is typically several orders of magnitude. Fundamental factors such as heat transfer, mass transfer, and the like can change in unpredictable ways, causing undesirable performance and sometimes necessitating design changes.

Second, as biomass-refining plants increase in size, a point is reached wherein the cost of transporting large quantities of biomass can cause the operating costs to be excessive. This is especially true for ultra-low-density biomass, such as straws and grasses, but is also true for low-density wood feedstocks. Typical approaches in the industry balance the cost of biomass transportation with economies of scale, implying a necessary trade-off.

Third, large-scale installations invariably require primarily engineered systems that cannot benefit from the standardization and utilization of mass-production techniques that can be applied to modular designs.

Modularization may be viewed as the grouping together of a set of units, or modules, to achieve a specific function (Schug and Realff, 1996). The concept of modularity has shown development in a range of areas, including pump design (Chynoweth, 1987); space modules (Cooper, 1990); oil drilling platforms (North, 1995); and manufactured parts (Sorokin, 1989). The purposes of development in these areas include faster lead times and flexibility of operation. Also, modularization may reduce the total amount of engineering development time and expense for each facility and for subsequent designs. Other noted benefits are an increase in the number of designs through combinations of modules and rapid deconstruction and reconstruction of modular systems (Schug and Realff, 1996).

A significant portion of biomass feedstock costs—especially from forests—can be attributed to the handling associated with moving them from their point of production to their end point of conversion or end-use (Sokhansanj, 2002). Traditionally, handling includes harvesting, chipping, loading onto trucks, and transportation to the end-use point. Handling solid forms of biomass is expensive for a number of reasons, including the number of operations required and the low bulk density of the feedstocks (Badger, 2002), which cause high transportation costs.

There exists a desire to overcome the large expenses associated with biomass handling. One way to minimize handling expenses is to reduce and/or optimize average transport distances for feedstock to conversion units. Therefore, methods and systems are necessary to determine an optimal number and distribution of modular units spatially located within a region of land.

In view of the aforementioned needs in the art with respect to modularity and distribution, what are especially needed are biomass-to-syngas methods and systems that are flexible, efficient, scalable, and ultimately cost-effective at virtually any scale of operation.

SUMMARY OF THE INVENTION

The present invention addresses the needs described above. In one aspect, the invention provides a method of distributing modular units within a specified region of land, wherein the modular units can convert a carbon-containing feed material into a mixture comprising syngas, the method comprising:

(a) determining a plurality of sources of carbon-containing feed material within the region of land;

(b) determining a desired feedstock capacity to be processed by the modular units within the region of land;

(c) calculating, for the plurality of sources of carbon-containing feed material within the region of land, transportation distances to a plurality of possible sites for modular units, thereby generating a feedstock transportation profile within the region of land;

(d) selecting a total number of modular units for the region of land, sufficient to be capable of processing an amount of carbon-containing feed material at least about equal to the desired feedstock capacity from step (b); and (e) distributing the modular units within the region of land based at least on information obtained in steps (a)-(d).

The carbon-containing feed material can be selected from the group consisting of timber harvesting residues, softwood chips, hardwood chips, tree branches, tree stumps, leaves, bark, sawdust, paper pulp, corn stover, wheat straw, rice straw, sugarcane bagasse, switchgrass, miscanthus, animal manure, municipal solid waste, municipal sewage, commercial waste, used tires, grape pumice, almond shells, pecan shells, coconut shells, coffee grounds, grass pellets, hay pellets, wood pellets, cardboard, paper, plastic, rubber, cloth, coal, lignite, coke, lignin, petroleum, and any combinations thereof.

In some embodiments, the distribution in step (e) utilizes an optimization routine performed on a computer, as further described herein. The optimization routine can include at least one constraint related to transportation distances of carbon-containing feed material sources to possible sites for the modular units. For example, transportation of carbon-containing feed material can be minimized. Methods can also determine at least one syngas-derived product transportation profile. The optimization routine can also include at least one constraint related to utilization of shared equipment or utilities.

In some embodiments, the total number of modular units selected in step (d) is at least 2. Also, in some embodiments, the distribution in step (e) comprises placement of at least one cluster, sometimes two or more clusters, each including two or more modular units.

In some embodiments, at least one modular unit is added to one or more pre-existing modular units within a region of land. In other embodiments, methods include moving at least one modular unit to a different location within the region of land. Or, methods can include removing at least one modular unit from the region of land.

In another aspect of the invention, a computing system is provided for distributing modular units within a specified region of land, wherein the modular units can convert a carbon-containing feed material into a mixture comprising syngas, the system comprising a computer having a processor, an area of main memory for executing program code under the direction of the processor, a storage device for storing data and program code and a bus connecting the processor, main memory, and the storage device; the code being stored in the storage device and executing in the main memory under the direction of the processor, to perform the steps (a)-(e) described herein with respect to a method aspect of the invention.

Another aspect of the present invention provides a method of converting a carbon-containing feed material into a mixture comprising syngas, the method comprising:

(a) providing one or more modular units;

(b) feeding a carbon-containing feed material into the one or more modular units;

(c) devolatilizing the carbon-containing feed material, thereby creating a solid phase and a gas phase; and (d) steam reforming the solid phase and the gas phase to produce syngas.

Again, the carbon-containing feedstock can be any known material that contains some carbon, for example (but not limited to) the feedstock materials recited herein above.

In some embodiments of this aspect, step (a) comprises providing a plurality of modular units capable of being connected to, and disconnected from, each other. The amount of carbon-containing feed material capable of being converted can be adjusted by adding units to or subtracting units from the plurality of modular units.

In some embodiments, methods further include generating electrical power and/or heat from at least some of the syngas. In other embodiments, or in combined embodiments, a liquid product is produced from some of the syngas. The liquid product can be, for example, methanol, ethanol, propanol, and/or butanol. In other embodiments, pyrolysis liquids are produced from the mixture comprising syngas. These fuels can be used to power an internal combustion engine, or they can be combined with at least one hydrocarbon not produced from the syngas, thereby creating a liquid-fuel blend that can be combusted to power an internal combustion engine or another type of engine.

Another aspect of the invention describes a system comprising a spatially distributed plurality of modular units for converting carbon-containing feed material into a mixture comprising syngas, each modular unit comprising:

(a) a feed inlet for carbon-containing feed material;

(b) a vessel for devolatilizing the carbon-containing feed material, capable of creating a solid phase and a gas phase;

(c) a vessel for steam reforming the solid phase and the gas phase, capable of producing syngas; and (d) at least one outlet for a mixture comprising syngas.

In some system embodiments, the modular units are capable of being connected to, and disconnected from, each other. The modular units can be portable. In some embodiments, the plurality of modular units comprises one or more clusters, each cluster including at least two modular units.

A system of the invention can further comprise a server computer linking the plurality of modular units, wherein the server computer is capable of performing calculations and sending output data across a network. The data can be associated with one or more packets of information selected from the group consisting of feedstock availability, feedstock composition, feedstock quality, feedstock price, operating parameters of each modular unit, and operating performance of each modular unit. An optimization routine can be provided in the system, where the routine can calculate parameters such as yield, selectivity, conversion, operating cost, revenue, and profit.

In certain embodiments, a system can include a first modular unit and a second modular unit, wherein the second modular unit can be installed while the first modular unit remains substantially capable of functional operation.

A system can include a reactor for producing a product from at least some of the syngas. The product can be methanol, ethanol, 1-propanol, 1-butanol, or some other alcohol, alkane, olefin, or oxygenate. Pyrolysis liquids can also be produced from the mixture comprising syngas. Or, the syngas can generate power, including electrical power, and/or heat. In some systems, at least two modular units are connected to the reactor to convert at least some of the syngas into a product.

These and other embodiments, features, and advantages of the present invention will become more apparent to those skilled in the art when taken in conjunction with the following more detailed description of the invention.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

The present invention provides methods and systems to utilize modular units for converting carbon-containing feed materials into useful products, such as syngas and derivatives of syngas. The present invention further provides methods and systems to determine an optimal number and distribution of modular units spatially located within a region of land. As used herein, "$C_2$-$C_4$ alcohols" means one or more alcohols selected from ethanol, propanol, and butanol, including all known isomers of such compounds.

"Biomass" for the purposes of the present invention is any material not derived from fossil resources and comprising at least carbon, hydrogen, and oxygen. Biomass includes, for example, plant and plant-derived material, vegetation, agricultural waste, wood waste, paper waste, animal-derived waste, and municipal solid waste. The present invention can also be used for carbon-containing feedstocks other than biomass, such as a fossil fuel (e.g., coal or petroleum). Thus, any method or system described herein in reference to biomass can alternatively be used with any other carbon-containing feed material.

The methods and systems of the invention can accommodate a wide range of feedstocks of various types, sizes, and moisture contents. In various embodiments of the invention, carbon-containing feedstocks can include one or more materials selected from timber harvesting residues, softwood chips, hardwood chips, tree branches, tree stumps, leaves, bark, sawdust, paper pulp, corn stover, wheat straw, rice straw, sugarcane bagasse, switchgrass, miscanthus, animal manure, municipal solid waste, municipal sewage, commercial waste, used tires, grape pumice, almond shells, pecan shells, coconut shells, coffee grounds, grass pellets, hay pellets, wood pellets, cardboard, paper, plastic, rubber, cloth, coal, lignite, coke, lignin, and/or petroleum. Mixtures of any of these feedstocks can be used. Mixtures can be accomplished by blending prior to feeding, co-feeding several feedstocks, or by some other means. A person of ordinary skill in the art will readily appreciate that the feedstock options are virtually unlimited.

According to the present invention, selection of a particular feedstock or feedstocks is not regarded as technically critical, but is carried out in a manner that tends to favor an economical process. Typically, regardless of the feedstocks chosen, there can be (in some embodiments) screening to remove undesirable materials. The feedstock can optionally be dried prior to processing. There can also be, but need not be, reduction of particle size prior to conversion of the biomass to syngas. Particle size, however, is not regarded as critical to the invention.

For the purposes of the present invention, "devolatilization" of biomass means that some light gases as well as volatile organic hydrocarbons are both released from the biomass. "Reforming" or "steam reforming" refers to the production of syngas when steam is the reactant. "Partial oxidation" refers to the production of syngas when oxygen is the reactant. "Gasification" generally refers to the production of a mixture of at least CO, $CO_2$, and $H_2$, and can include one or more of devolatilization, reforming, or partial oxidation, as well as some amount of pyrolysis, combustion, water-gas shift, and/or other chemical reactions.

A "modular unit" or "module" means an apparatus comprising means for converting biomass into syngas, said apparatus capable of either operably standing alone or of being operably connected with at least one other modular unit. A "cluster" of modular units is two or more of said units coupled together so as to increase the feedstock capacity of the system. In various embodiments, clusters can contain 2, 3, 4, 5, 6, 7, 8, 9, 10 or more modular units. A "modular system" is characterized by one or more modular units or clusters according to the present invention.

According to some embodiments, the invention provides for rapid deconstruction and reconstruction of modular units. In some particular embodiments, units are mobile. Mobility, or portability, allows the modular units to be moved to another location within the region of land or to a different geography. In certain embodiments, modules can be added to, or taken out of commission from, other unit(s) without significant interruption to the operation of said other unit(s). Portability of modules can be beneficial when feedstock availability or costs change, or due to a variety of permitting, labor, or utility issues. Portable modular units, after being moved, can be connected with an existing modular unit or cluster, or installed as a stand-alone unit.

Figure 1:
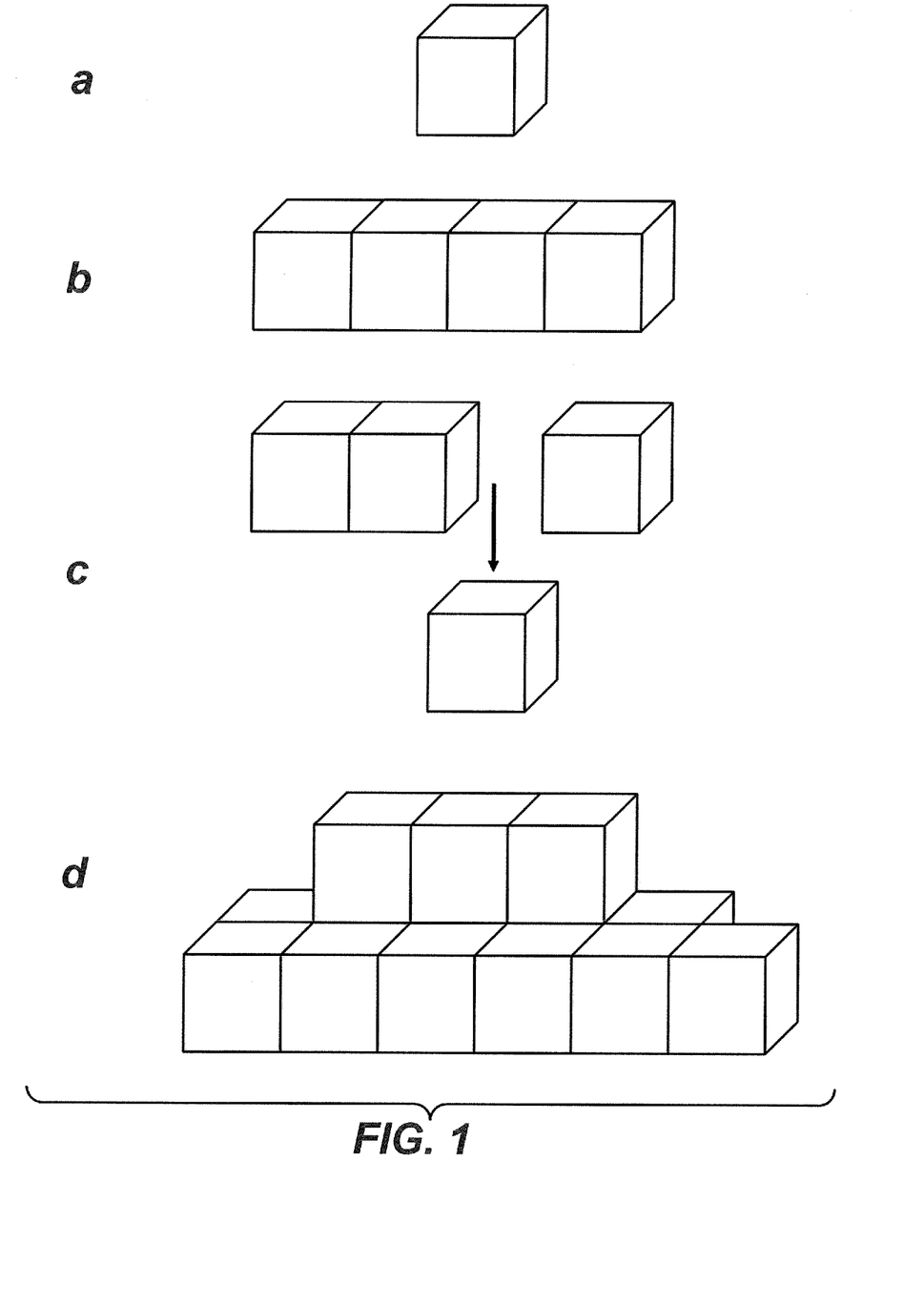
FIGS. 1A-1D are diagrams depicting various numbers and configurations of modular biomass-to-syngas units and clusters, for non-limiting illustration purposes only.

FIGS. 1A-1D illustrate various numbers and configurations of modular biomass-to-syngas units and clusters. Each cube is meant to represent a modular unit; the cubic representation is merely for convenience and does not limit or relate to any specific design or physical configuration. Process streams and equipment configuration details are omitted for the purpose of this drawing. FIG. 1A shows a single, stand-alone modular unit. FIG. 1B shows a cluster consisting of 4 modular units in close connection. FIG. 1C represents the removal of one of the modular units from the scenario depicted in FIG. 1B, wherein the remaining modular units can remain functional. Finally, FIG. 1D shows a cluster consisting of 14 biomass-to-syngas modular units functionally connected. These drawings are merely illustrative.

In certain embodiments, modular design according to the invention can provide several benefits such as: easier debottlenecking and process modification, shorter delivery times, and lower engineering costs. Modularity can provide advantages for maintenance, as maintenance need not be performed on the entire system but rather can be focused on specific modules. In some embodiments, modular design can reduce the total amount of regulatory approval time and expense: an item may be approved for one system and used for several others without undergoing additional approval.

In preferred embodiments, a modular-design system may be adjusted to meet changing market demands, and/or can be designed for expansion. A bottleneck condition could be removed simply by replacing a modular unit with a higher-capacity equivalent, or by installing and connecting additional modules. For other performance-requirement changes, it can be possible to remove some modular units and add others to allow the system to meet the new demands.

A plurality of modular units can also provide certain operational advantages. When a system comprises m modular units and a major process upset occurs in one unit (decreasing the syngas yield, for example), the impact is generally limited to 1/m of the effect that might otherwise occur if a single facility was employed. Essentially, process risk is distributed. The probability of an upset may or may not be lower than for a larger plant, but the impact of an upset should be dampened.

Some embodiments of the present invention provide automated, modular systems for converting solid carbonaceous materials to syngas. Generally speaking, modern microprocessor control can be coupled to methods of the invention to result in systems requiring reduced operator attention. In some embodiments, the entire system can be controlled by an embedded, programmable automation controller, which in turn can be controlled by a remotely located computer, using a local area network or the Internet for communication. Embedded in the control program can be mathematical algorithms that cause the system to properly react to changing process conditions in the same or similar manner as an expert human operator might react.

Advanced analytical techniques can be used in certain embodiments. For example, mass spectrometers can measure real-time gas concentrations and aid in optimizing the operation of the modular units. As another example, feedstock composition can be measured dynamically using Near Infrared (NIR) spectroscopy and Projection to Latent Structures (PLS) multivariate analysis for the rapid chemical characterization of biomass, according to a method developed at the National Renewable Energy Laboratory (Hames et al., 2003). The NIR/PLS technique can be employed to measure not only the intrinsic C/H/O ratios in the feedstock but also the ash and moisture content, providing useful data for tuning gasification, reforming, and/or partial-oxidation conditions and recycle strategies within the modular units.

In some embodiments, some or all of the modular units within the region of land can be interconnected by a computer network. The computer network can be any type of network as is known, such as (but not limited to) a local area network, the Internet, radio, telephone land lines, a cellular network, or another type of network. A satellite-based network such as the Global Positioning System can be used in some embodiments to track locations of modular units and/or feedstock sources, and generally to gather information to help optimize distribution and operation of the modular biomass-to-syngas units.

When a computer network is employed, operating data can be shared between modular units and/or with a central server. The operating data can include one or more parameters selected from: feedstock composition; concentration profiles of chemical species such as $CO$, $H_2$, $O_2$, $CO_2$, $H_2O$, or other species; temperature profile; pressure profile; average residence times; residence-time distribution; product selectivities; feedstock conversion; energy-balance data; and mass-balance data including recycle flows. The operating data obtained dynamically for a certain feedstock or a certain set of conditions in a first modular unit can be sent over a network to a second modular unit (or more than one other unit) so that said units can optionally adjust operating parameters accordingly. Preferred techniques of utilizing such data include statistical analysis of variance, to ascertain which effects are real and which are random process noise.

In some embodiments, this type of data communication can be advantageous to preemptively optimize conditions and increase overall efficiencies. Underperforming modular units can be identified in the context of the average performance across the region of land or within certain clusters using similar feedstocks. For instance, a system average could be computed for a certain parameter, and then a deviation could be calculated from the average for each modular unit. Changes could then be made according to preset instructions.

Other data relating to business strategy can be communicated across the computer network. Such data can include dynamic supply and demand for syngas or derivatives of syngas, dynamic pricing information for local feedstocks, and the like. One use of such data is, for example, adjusting feed rates for different modular units even if the overall system feed rate stays substantially the same.

Feedstocks and products can be transported within a region of land by any known means, such as by truck, train, ship, barge, tractor trailer, or any other mode of transport. In some embodiments, the region of land includes pipelines for feedstocks, product intermediates, or final products, similar to existing pipelines serving the petrochemical industry. Specifically, the region of land could include syngas pipelines; pipelines for mixed alcohols, crude ethanol, and/or purified ethanol; and/or pipelines for other derivatives of syngas. Additionally, it is envisioned that pipelines could be constructed and made available to transport feedstock in the form of slurried biomass, fluidized biomass in a vapor or liquid carrier, biomass-derived pyrolysis liquids, or in another form that can be moved conveniently in a pipeline. The distribution of modular units can be integrated with the network of pipelines. Any of these pipelines can be partially or wholly underground, and they can extend beyond the region of land comprising the modular units. Such pipelines can be in communication with the computer network serving the system(s) of the invention.

In some aspects of the present invention, distribution methods and systems are provided to distribute modular units within a specified region of land, wherein the modular units can convert biomass into a mixture comprising syngas.

"Region of land," according to the invention, means an area of land of any size that includes at least one source of biomass feedstock, either natively or imported. The region of land need not be continuous as shown in exemplary FIG. 2; rather, the region could be defined by several discrete areas that, taken together, specify a region over which to distribute modular units. Additionally, a region of land according to the present invention can be static (predetermined), or it can be dynamic with expanding or contracting boundaries. However, at each instance of applying the methods of the invention to determine an optimal or preferred distribution and number of modular units, the region of land of interest is preferably substantially specified.

The region of land, according to the invention, can be of essentially any shape and size. To characterize the size (area) of the region of land, reference can be made to an area, in units such as acres or square miles; oftentimes, in the art, reference is instead made to a radius or diameter of a circle whose area equals the area of the region of interest, regardless of the actual shape of said region. This approach is common because, when evaluating costs for biomass transportation to a processing plant, an economic transportation distance is commonly associated with the plant. The area described by that distance constraint is a circle.

The region of land, in some embodiments of the present invention, could be as small as a land area on the order of an acre or less. The area of the region could be about 1, 10, 100, or 500 acres, for example, as might be found on a small harvesting operation or farm. A circle whose area is 500 acres is defined by a diameter of about 1 mile. In some embodiments, the area of the region of land can be defined by an equivalent diameter on the order of 1 mile, 10 miles, 100 miles, 1000 miles, or more. In certain embodiments, the region of land is the entire United States, whose equivalent diameter is about 2200 miles. The region of land is not limited to the United States of America but can also include parts or all of North America, South America, Europe, Asia, Africa, and Antarctica. In a particular embodiment, methods and systems of the invention are provided for the entire world.

The distribution methods and systems provided by the present invention comprise the following steps:

(a) determining a plurality of sources of biomass (or another carbon-containing feedstock) within a region of land;
(b) determining a desired biomass feedstock capacity to be processed by the plurality of modular units within the region of land;
(c) calculating, for the plurality of sources of biomass within the region of land, transportation distances to a plurality of possible sites for modular units or clusters of modular units, thereby generating a feedstock transportation profile within the region of land;
(d) selecting a total number of modular units or clusters of modular units for the region of land, sufficient to be capable of processing an amount of biomass feedstock at least about equal to the desired feedstock capacity from step (b); and
(e) distributing the modular units within the region of land based at least on information obtained in steps (a)-(d).

Figure 2:
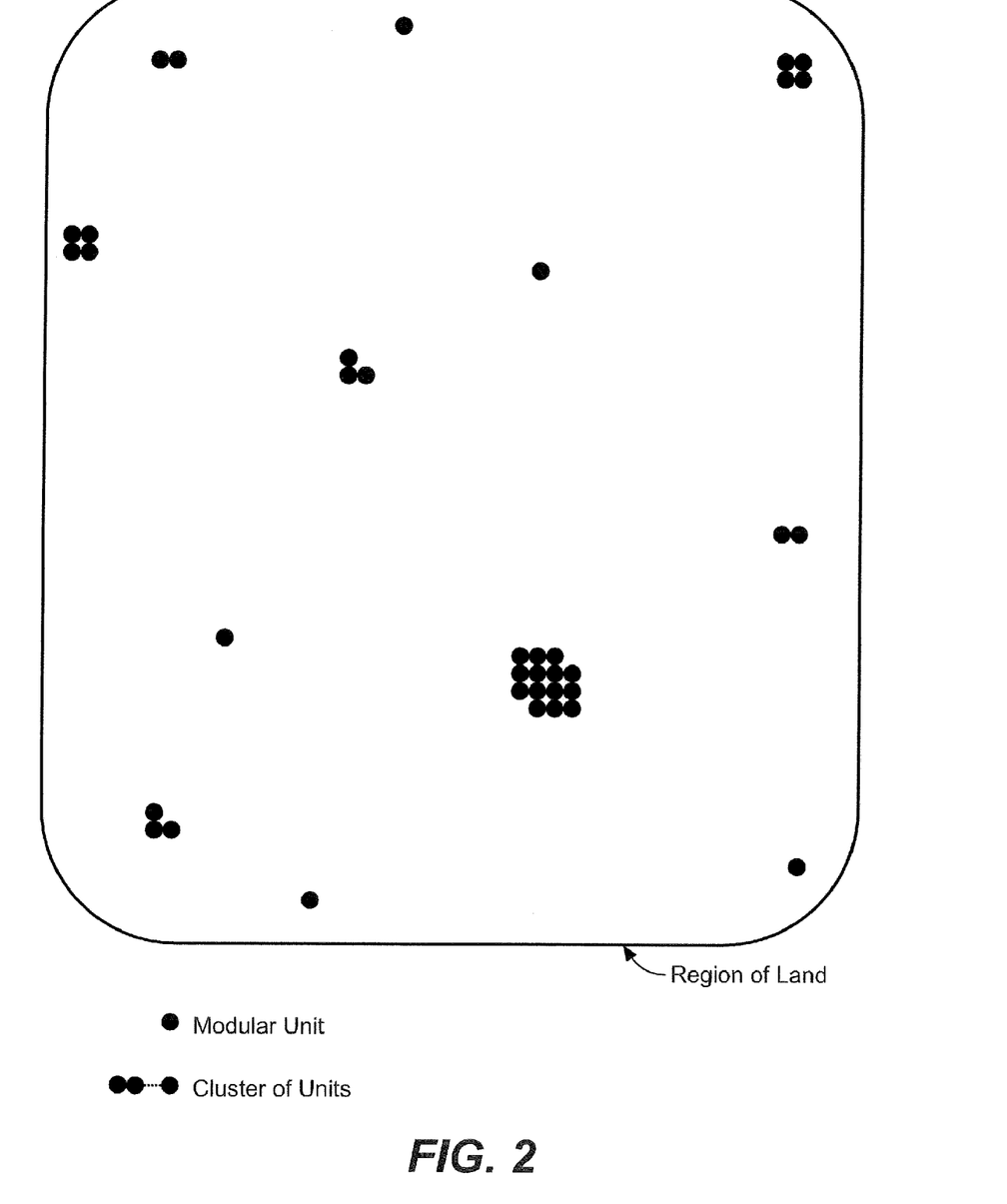
FIG. 2 is a map illustrating an exemplary distribution of modular biomass-to-syngas units within a region of land.

FIG. 2 illustrates an exemplary distribution of modular biomass-to-syngas units within a certain region of land. In this diagram, circles represent single modular units, and clusters of units are shown by two or more circles in close connection. The circular representation is merely for convenience and does not limit or relate to any design or specific physical or spatial configuration. FIG. 2 shows 12 nodes (defined as any location that actually contains one or more modules). There are 5 single-module nodes and 7 clustering nodes, with the largest cluster being constructed of 14 modular units. FIG. 2 denotes a system architecture consisting of a total of 37 modular units.

With reference to FIG. 2, and according to the present invention, one can select a region of land (the outer boundary of the diagram) and determine at least one source of biomass within that region. A desired biomass processing capacity can then be selected. For at least one source of biomass within the region of land, transportation distances can be calculated or estimated to a plurality of possible sites for modular units or clusters of such units. These transportation distances, and possibly other available information, can generate a feedstock transportation profile within the region of land. One can then select a total number of modular units or clusters of modular units for the region of land, sufficient to be capable of processing the desired amount of biomass, or more (if spare units are desired, for example). The desired overall biomass capacity can be optionally adjusted at any time, including after construction of one or more modules, during start-up, during operation, or at any other time. One can distribute the modular units within the region of land based at least on this information, and possibly other factors, as will be appreciated. FIG. 2 is one such distribution of units and nodes.

These distribution methods enable the placement of modular units near biomass sources, minimizing transportation energy and thereby increasing the yield of syngas (and/or derivatives of syngas) per amount of energy expended. Modular units can be readily located where biomass is most plentiful, preferably avoiding the transport of biomass to a central processing site. The modularity that characterizes the systems of the invention allows overall feedstock capacity to grow as more biomass becomes economically available, according to supply and demand across the region of land.

According to the methods and systems of the present invention, the feedstock capacity can vary widely, depending on the size of individual modular units and the number of units utilized. Feedstock capacity can be selected based on one or more criteria selected from present or future supply and demand of biomass; present or future supply and demand of syngas; present or future supply and demand of syngas derivatives, such as ethanol; labor availability; permitting; and so on.

The modular units of the invention are not limited to any particular feedstock capacity, as will be appreciated. For purposes of illustration, the capacity of each individual modular unit can be less than one dry ton (T) of biomass per day (d), or on the order of 1, 10, 100, 1000, or more dry T/d. Preferably, the modular capacity is between about 10-1000 dry T/d, and more preferably about 50-500 T/d. Economics, including local feedstock availability, will generally dictate the design selection of feedstock capacity for each modular unit. In some embodiments, the modular units are designed to each have the same biomass capacity.

Likewise, the invention is not limited to any particular overall feedstock capacity for systems comprising a plurality of modular units and/or clusters of such units. Within a specified region of land, the order of magnitude of the overall (combined) feedstock capacity, according to the present invention, can be 1, 10, $10^2$, $10^3$, $10^4$, $10^5$ dry T/d or even higher. Also, it should be noted that within a certain system, there is no requirement that individual feedstock capacities be the same.

Also, capacities can be specified in a different manner than dry tons per day, including but not limited to actual (or wet) tons biomass per day, ash-free wet or dry tons per day, tons of carbon per day, tons of hydrogen per day, pounds of any of these quantities per day, moles of any of these quantities per day, and any other time label such as second, week, month, year, operating year, harvest year, and so on.

The syngas produced in the distributed, modular units as described according to the present invention can be utilized in a number of ways. Syngas can generally be chemically converted and/or purified into hydrogen, carbon monoxide, methane, graphite, olefins (such as ethylene), oxygenates (such as dimethyl ether), alcohols (such as methanol and ethanol), paraffins, and other hydrocarbons.

The syngas produced according to the methods and systems of the invention can further produce: diesel fuel, gasoline, waxes, or olefins by Fischer-Tropsch chemistry; methanol, ethanol, and mixed alcohols (such as $C_2$-$C_4$ alcohols) by a variety of catalysts; isobutane by isosynthesis; ammonia by hydrogen production followed by the Haber process; aldehydes and alcohols by oxosynthesis; and many derivatives of methanol including dimethyl ether, acetic acid, ethylene, propylene, and formaldehyde. In certain preferred embodiments, the syngas is converted to high yields of alcohols, particularly ethanol. As is known, syngas can also be fermented to a mixture comprising ethanol using microorganisms, including bacteria such as *Clostridium ljungdahlii*.

In some embodiments, multiple modular units according to the present invention can be connected to a reactor to convert syngas to chemical and/or fuel products. "Multiple modular units" means 2, 3, 4, 5, 6, 7, 8, 9, 10 or more such units. Further, multiple units can be grouped into one or more clusters, each comprising one or a plurality of units; or multiple units can mean several distributed units across a region of land. In any case, the syngas output of any number of modular units can be (but need not be) combined before or after purification, conditioning, or other steps. The combined syngas can then be fed into one or more reactors to produce chemicals and/or fuels.

Certain embodiments of the invention can be further understood by reference to FIGS. 3-13, which depict variations and embodiments of a process and apparatus for producing syngas and, in turn, alcohols from a carbon-containing feed material such as biomass.

Figure 3:
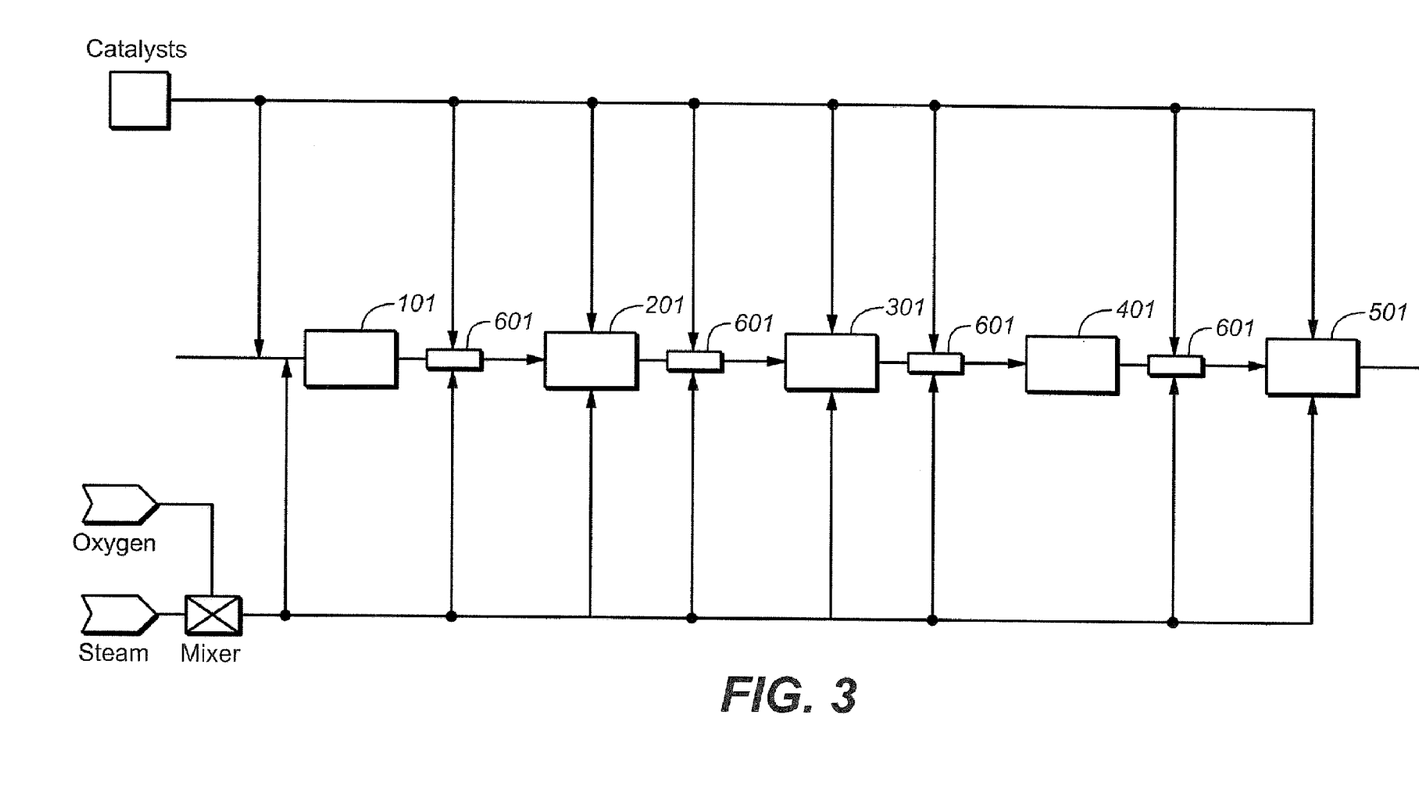
FIG. 3 shows a process flow for the production of syngas from any carbon-containing feed material, according to one variation of a process and apparatus that can be modularized and distributed.
Figure 4A:
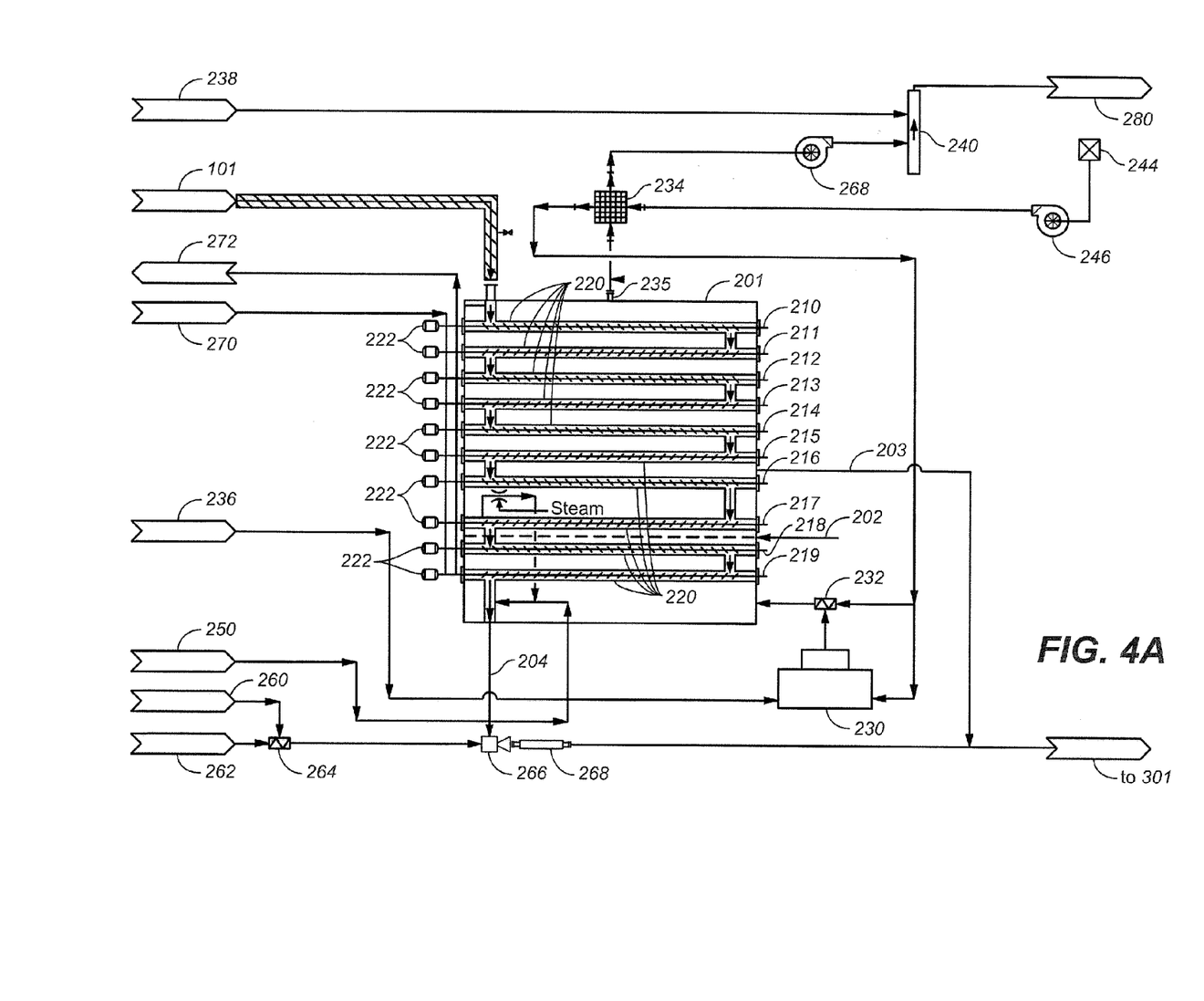
FIG. 4A shows a process flow for a two-stage devolatilization unit, according to one variation of a process and apparatus that can be modularized and distributed.
Figure 4B:
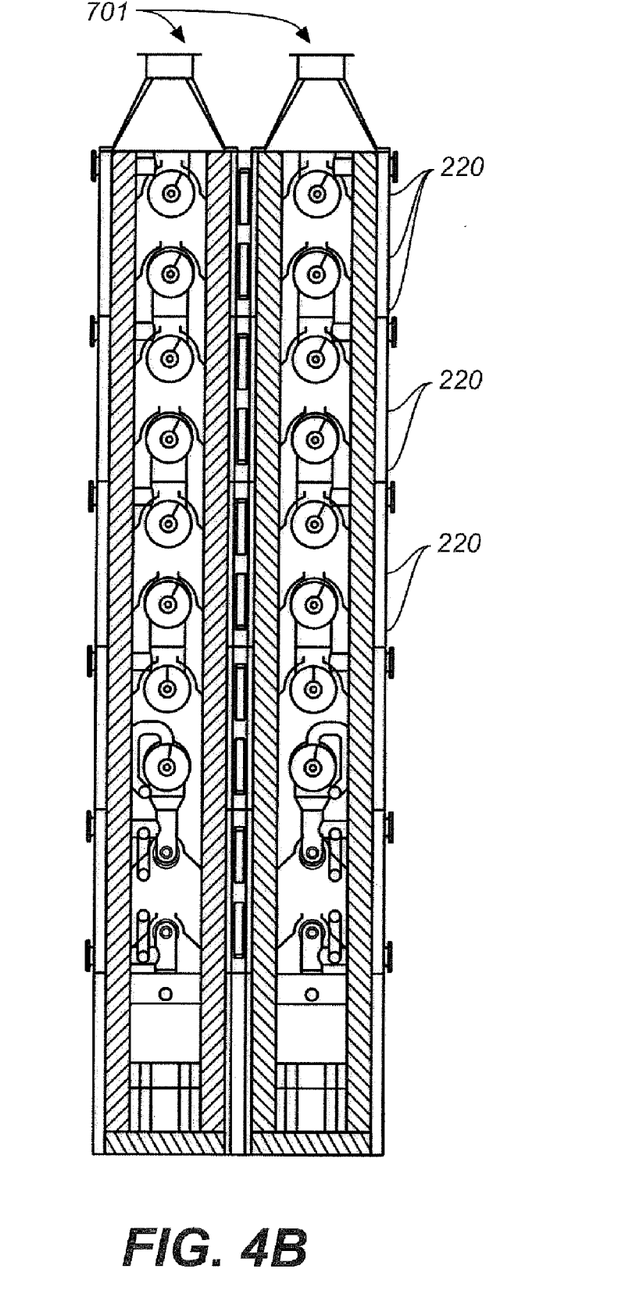
FIG. 4B shows a side view of the two-stage devolatilization unit shown in FIG. 2A.
Figure 5:
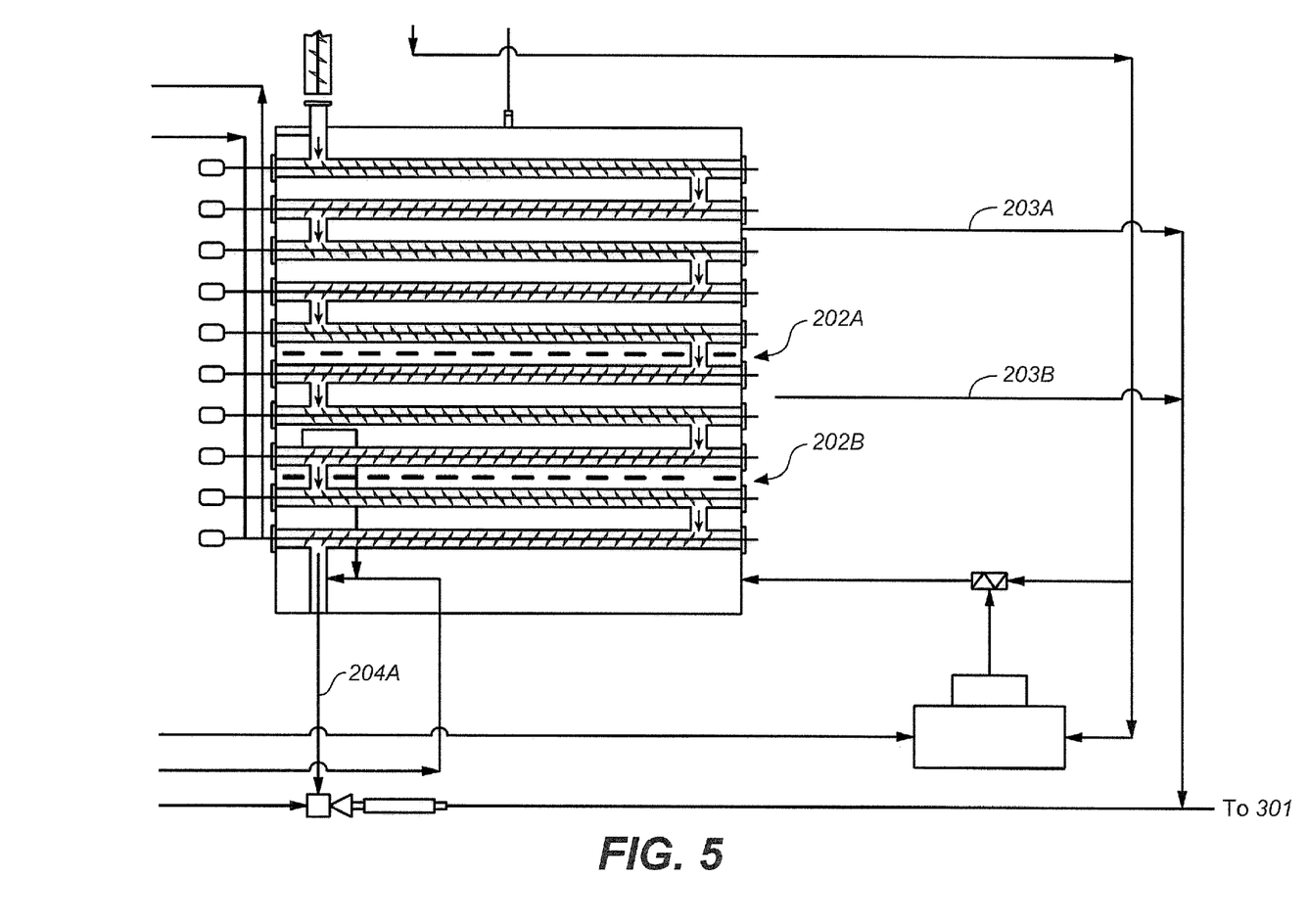
FIG. 5 shows a process flow for a three-stage devolatilization unit, according to one variation of a process and apparatus that can be modularized and distributed.
Figure 6:
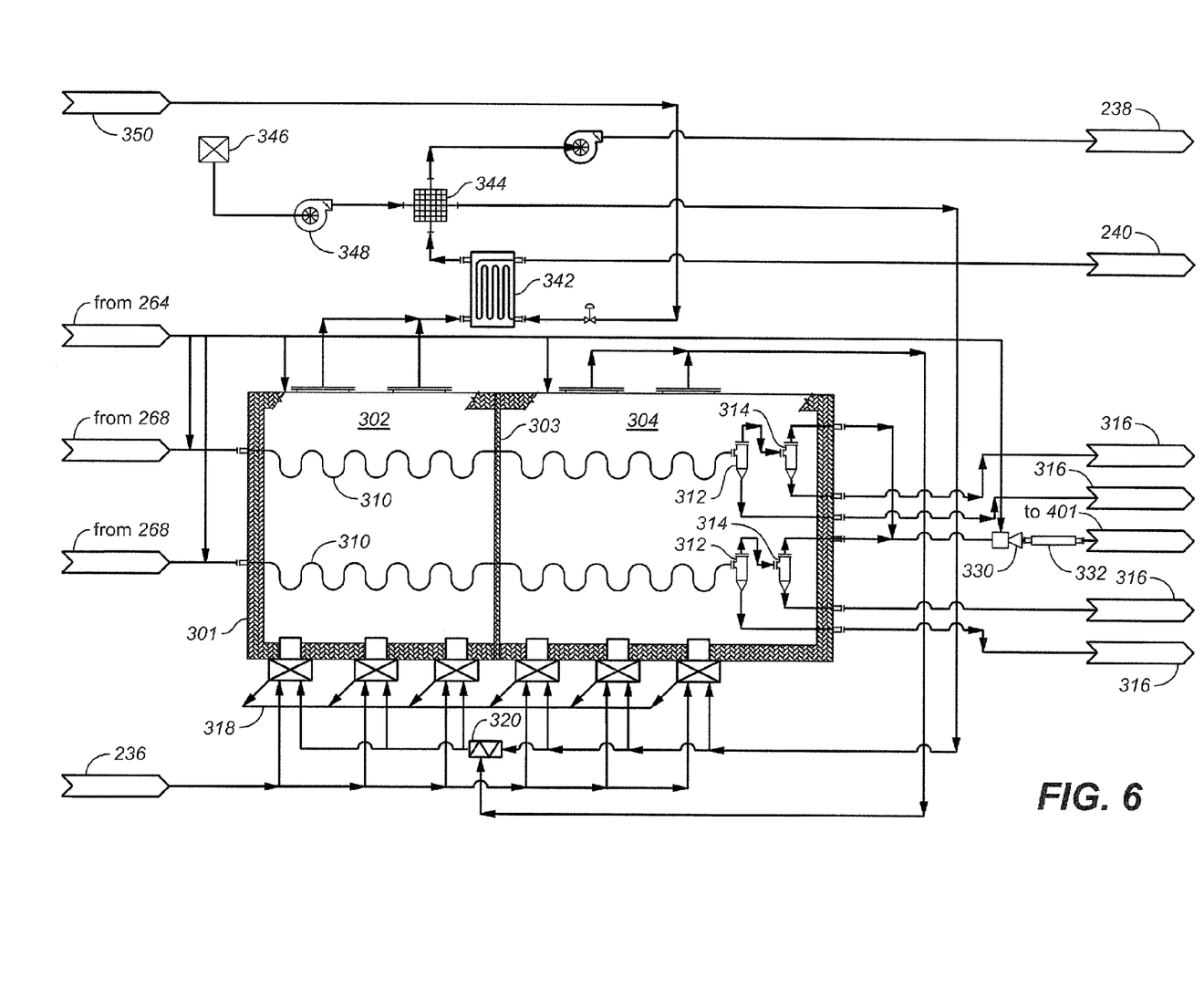
FIG. 6 shows a process flow for a reformer reactor, according to one variation of a process and apparatus that can be modularized and distributed.
Figure 7:
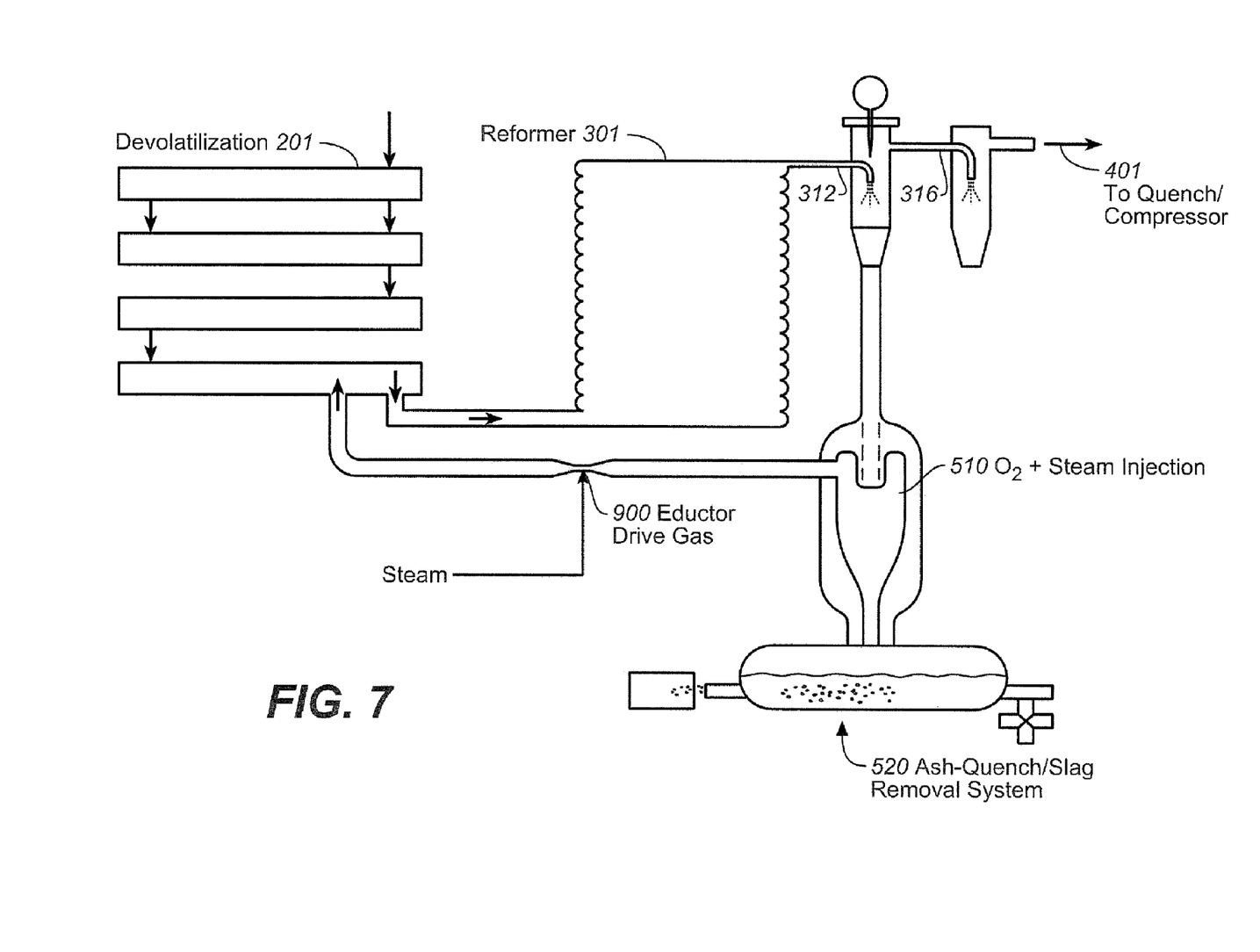
FIG. 7 shows a process flow for the injection of oxygen and steam into syngas that is recycled back to the devolatilization unit, according to one variation of a process and apparatus that can be modularized and distributed.
Figure 8:
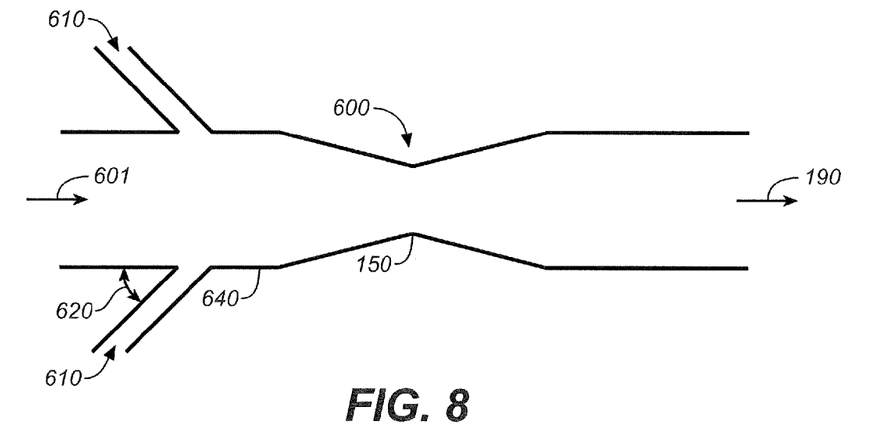
FIG. 8 shows an eductor that can be employed in a modularized process and apparatus, in some embodiments.

FIG. 3 shows a process flow for the production of syngas from any carbon-containing feed material, according to one variation of a process and apparatus that can be modularized and distributed. FIG. 4A shows a process flow for a two-stage devolatilization unit, according to one variation. FIG. 4B shows a side view of the two-stage devolatilization unit shown in FIG. 2A. FIG. 5 shows a process flow for a three-stage devolatilization unit, according to one variation of a process and apparatus that can be modularized and distributed. FIG. 6 shows a process flow for an exemplary reformer reactor. FIG. 7 shows a process flow for the injection of oxygen and steam into syngas that is recycled back to the devolatilization unit, according to one variation of a process and apparatus that can be modularized and distributed. FIG. 8 shows an eductor that can be employed in some embodiments.

Figure 9:
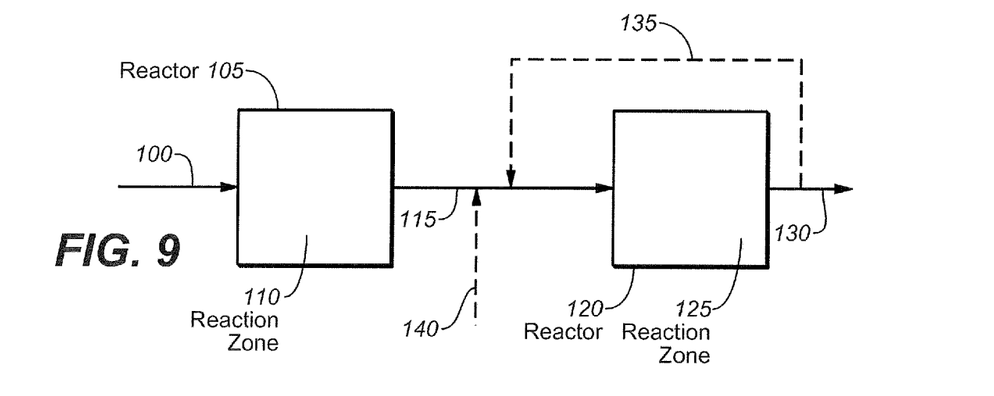
FIG. 9 shows a process flow for producing methanol and ethanol from syngas using two reactors in sequence, according to one variation of a process and apparatus that can be modularized and distributed.
Figure 10:
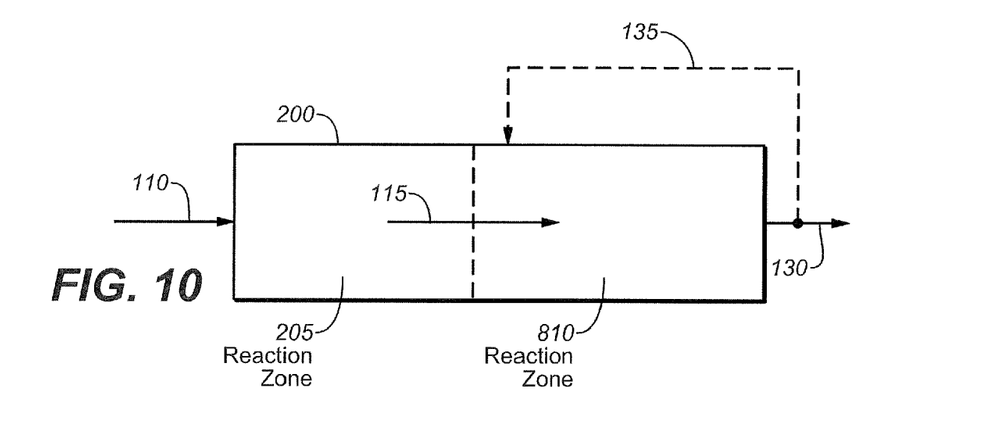
FIG. 10 shows a process flow for producing methanol and ethanol from syngas using two reaction zones in sequence in a single reactor, according to one variation of a process and apparatus that can be modularized and distributed.
Figure 11:
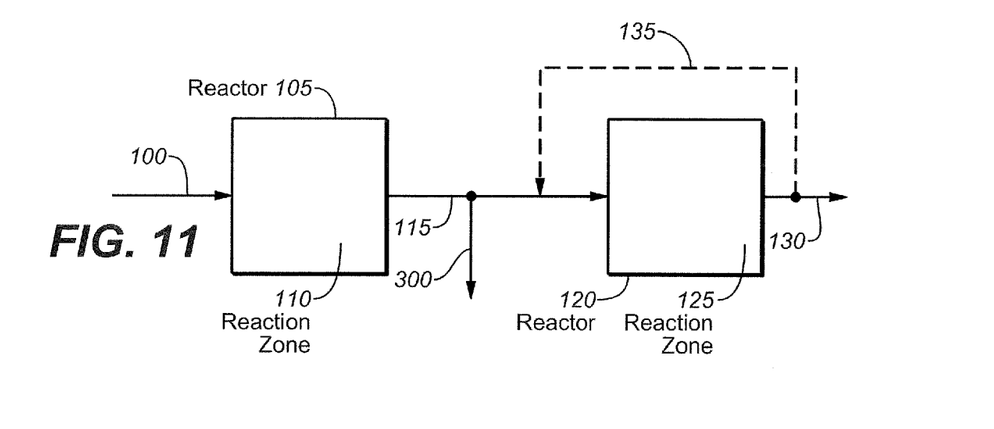
FIG. 11 shows a process flow for producing methanol and ethanol from syngas using two reactors in sequence, with at least some of the methanol produced in the first reactor diverted from the second reactor, according to one variation of a process and apparatus that can be modularized and distributed.
Figure 12:
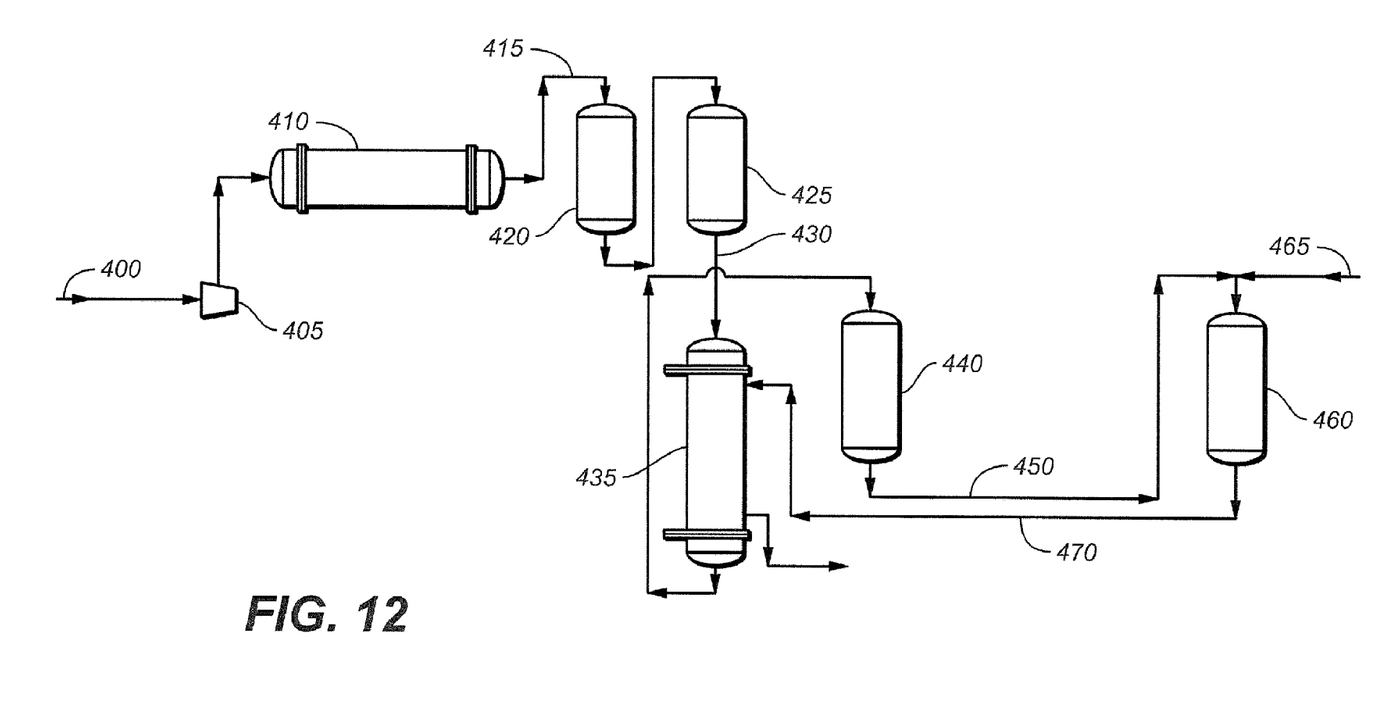
FIG. 12 shows a process flow for producing methanol and ethanol from syngas using two reactors in sequence according to another variation.
Figure 13:
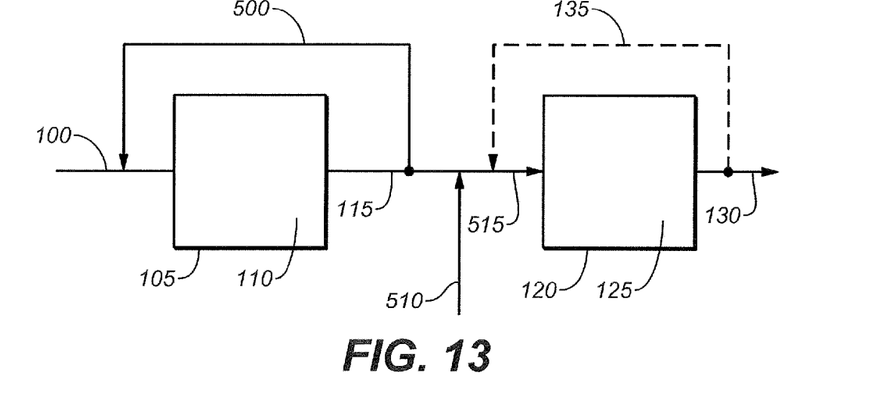
FIG. 13 shows a process flow for producing methanol and ethanol from syngas using two reactors in sequence, with the first reactor producing methanol in high yield for conversion to ethanol in the second reactor.

FIG. 9 shows a process flow for producing methanol and ethanol from syngas using two reactors in sequence, according to one variation of a process and apparatus that can be modularized and distributed. FIG. 10 illustrates a process flow for producing methanol and ethanol from syngas using two reaction zones in sequence in a single reactor. FIG. 11 shows a process flow for producing methanol and ethanol from syngas using two reactors in sequence, with at least some of the methanol produced in the first reactor diverted from the second reactor, according to another variation. FIG. 12 shows an embodiment for producing methanol and ethanol from syngas using two reactors in sequence according to yet another variation. FIG. 13 shows a process flow for producing methanol and ethanol from syngas using two reactors in sequence, with the first reactor producing methanol in high yield for conversion to ethanol in the second reactor, according to another non-limiting variation that can be modularized and distributed according to the present invention.

The syngas produced according to the methods and systems of the invention can also be converted to energy. Syngas-based energy-conversion devices include a solid-oxide fuel cell, Stirling engine, micro-turbine, internal combustion engine, thermo-electric generator, scroll expander, gas burner, thermo-photovoltaic device, or gas-to-liquid device. In some cases, the output syngas of two or more reactors can be combined to supply syngas to downstream subsystems comprised of syngas coolers, syngas cleaners, and syngas-based energy-conversion devices.

In some embodiments of the present invention, pyrolysis liquids are produced from a carbon-containing feed material. For present purposes, "pyrolysis liquids" can include aldehydes, ketones, acids, alcohols, phenols, furans, sugars, lignin, carbon, and water, or any other component derived from the pyrolysis of a carbon-containing feed material. In these embodiments, a carbon-containing feed material is introduced into the one or more modular units, followed by devolatilization to create a solid phase and a gas phase comprising syngas. Pyrolysis liquids can be captured directly from one or both phases, in certain embodiments. In other embodiments, one or both phases can be directed to a separate reactor to carry out additional chemical reactions (e.g., polymerization) to generate additional pyrolysis liquids.

It is contemplated, in certain aspects, that the distribution systems and methods of the present invention can be applied to modular biomass conversion in general, regardless of final products. For example, the methods of determining preferred or optimal distributions of modular units can be used for units that convert biomass into sugars that are capable of being fermented into ethanol, butanol, acetic acid, lactic acid, citric acid, or any other known fermentation product. There are a variety of technologies known in the art to fractionate, hydrolyze, or otherwise pretreat biomass so that cellulose and preferably also hemicellulose (if present) can be fermented, directly or after saccharification, into products.

It is known that biomass typically contains significant quantities of lignin, which cannot be readily fermented to products. In certain embodiments, the distribution systems and methods of the present invention are useful for distributing biomass-conversion modular units wherein lignin is recovered. However, it can be particularly desirable to convert the lignin contained in the starting biomass into syngas, so that it can then be flexibly converted into any of the fuels and chemicals described above. In the present invention, modular systems and methods are provided that can convert the lignin (as well as the rest of the biomass) into syngas. It is also envisioned that a modular unit could be designed to separate lignin from biomass and convert the carbohydrates to fermentation products, while turning the lignin-rich residue into syngas.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are incorporated herein by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

REFERENCES

Badger, P. C., "Process cost analysis for biomass feedstocks," Oak Ridge National Laboratory, Environmental Sciences Division, Bioenergy Systems Group, Oak Ridge, Tenn. USA, Report ORNL/TM-2002/199, April 2002.

Chynoweth, E., "Mixing and matching modular pumps," *Process Engineering (London)*, Vol. 68, No. 9, 77-79, 1987.

Cooper, M., "Concept of adaptability in space modules," *Journal of Aerospace Engineering*, Vol. 3, No. 4, 235-240, 1990.

Hames, B. et al., "Biomass rapid analysis network," National Renewable Energy Laboratory, brochure NREL/FS-510-34724, October 2003.

North, R. B., "Universal modular platform," *Proceeding of the 9th Middle East Oil Show& Conference*, Vol. 2, 83-92, 1995.

Schug, B. W. and M. J. Realff, "Design of standardized, modular, chemical processes," *Computers & Chemical Engineering*, Vol. 20, S435-S441, 1996.

Sokhansanj, S., "Biomass feedstock engineering," Research Proposal 2002-2012, Oak Ridge National Laboratory, Environmental Sciences Division, Bioenergy Systems Group, Oak Ridge, Tenn. USA, 2002.

Sorokin, A. I. et al., "Modular technological processes in the manufacture of parts," *Soviet Engineering Research*, Vol. 9, No. 11, 95-97, 1989.

What is claimed is:

1. A method of converting a carbon-containing feed material into alcohols, said method comprising:
    (a) providing one or more modular units;
    (b) feeding a carbon-containing feed material into said one or more modular units;
    (c) devolatilizing said carbon-containing feed material in multiple-stage devolatilization reactors contained within each of said one or more modular units, thereby creating a solid phase and a gas phase;
    (d) steam reforming said solid phase and said gas phase to produce syngas within each of said one or more modular units;
    (e) producing, from at least a portion of said syngas, one or more alcohols selected from the group consisting of ethanol, propanol, and butanol within each of said one or more modular units; and
    (f) injecting oxygen and steam into at least a portion of said syngas to recycle said at least a portion of said syngas back to said multiple-stage devolatilization reactors.

2. The method of claim 1, wherein step (a) comprises providing a plurality of modular units capable of being connected to, and disconnected from, each other.

3. The method of claim 2, wherein the amount of carbon-containing feed material capable of being converted is adjusted by adding units to or subtracting units from said plurality of modular units.

4. The method of claim 1, wherein said carbon-containing feed material is selected from the group consisting of timber harvesting residues, softwood chips, hardwood chips, tree branches, tree stumps, leaves, bark, sawdust, paper pulp, corn stover, wheat straw, rice straw, sugarcane bagasse, switchgrass, miscanthus, animal manure, municipal solid waste, municipal sewage, commercial waste, used tires, grape pumice, almond shells, pecan shells, coconut shells, coffee grounds, grass pellets, hay pellets, wood pellets, cardboard, paper, plastic, rubber, cloth, coal, lignite, coke, lignin, petroleum, and any combinations thereof.

5. The method of claim 1, further comprising generating electrical power and/or heat from at least some of said syngas.

6. The method of claim 1, further comprising powering an internal combustion engine, at least in part, with said one or more alcohols.

7. The method of claim 1, further comprising combining said one or more alcohols with at least one hydrocarbon not produced from said syngas, thereby creating a liquid-fuel blend.

8. The method of claim 7, further comprising powering an internal combustion engine, at least in part, with said liquid-fuel blend.

* * * * *